US006225510B1

(12) United States Patent
Frenkel et al.

(10) Patent No.: US 6,225,510 B1
(45) Date of Patent: May 1, 2001

(54) PREPARATION OF DI-T-ALKYL PEROXIDES AND T-ALKYL HYDROPEROXIDES FROM N-ALKYL ETHERS

(75) Inventors: Peter Frenkel; Ted M. Pettijohn, both of Longview, TX (US); Lawrence R. Brecker, Armonk, NY (US)

(73) Assignee: Crompton Corporation, Greenwich, CT (US)

( * ) Notice: Subject to any disclaimer, the term of this patent is extended or adjusted under 35 U.S.C. 154(b) by 0 days.

(21) Appl. No.: 09/459,254

(22) Filed: Dec. 10, 1999

(51) Int. Cl.$^7$ .................................................. C07C 409/00
(52) U.S. Cl. ........................................... 568/558; 568/568
(58) Field of Search ...................... 568/558, 568

(56) References Cited

U.S. PATENT DOCUMENTS

| | | | |
|---|---|---|---|
| 2,845,461 | 7/1958 | Winkler | 260/610 |
| 3,825,605 | 7/1974 | Johnston | 260/632 |
| 4,296,263 | 10/1981 | Worrell | 568/910 |
| 4,406,254 | 9/1983 | Harris et al. | 44/56 |
| 4,810,809 | 3/1989 | Sanderson et al. | 549/529 |
| 5,095,164 | 3/1992 | Gabel et al. | 585/640 |
| 5,243,084 | 9/1993 | Cochran et al. | 568/571 |
| 5,288,919 | 2/1994 | Faraj | 586/578 |
| 5,312,998 | 5/1994 | Liotta, Jr. et al. | 568/578 |
| 5,314,511 | 5/1994 | Liotta, Jr. et al. | 44/322 |
| 5,345,009 | 9/1994 | Sanderson et al. | 568/909 |
| 5,371,298 | 12/1994 | Pourreau et al. | 568/578 |
| 5,399,777 | 3/1995 | Mueller | 568/569 |
| 5,420,357 | * 5/1995 | Faraj et al. | 568/578 |
| 5,488,176 | 1/1996 | Faraj | 568/588 |
| 5,488,178 | 1/1996 | Knifton et al. | 568/578 |
| 5,488,179 | 1/1996 | Knifton et al. | 568/578 |
| 5,866,712 | 2/1999 | Sanchez et al. | 560/170 |
| 5,939,592 | 8/1999 | Knifton et al. | 568/877 |

FOREIGN PATENT DOCUMENTS

| | | |
|---|---|---|
| 2400739 | 7/1975 | (DE). |
| 407840 | 1/1991 | (EP). |
| 438844 | 7/1991 | (EP). |
| 639564 | 2/1995 | (EP). |
| 860412 | 8/1998 | (EP). |
| 173171 | 2/1994 | (IN). |
| 3/190856 | 8/1991 | (JP). |

OTHER PUBLICATIONS

CA:76:71946 abs of Zh Prikl Kim (Leningrad) by Chizhov et al 44(12) pp 2692–2696, 1971.*

A.G. Davies, et al. "Organic Peroxides. Part IX", J. Chem Soc., 1958, 4637–4643.

N.A. Milas, et al "Studies in Organic Peroxides. V. t–Butyl Hydroperoxide", J. Amer. Chem. Soc. 1938, 60(10), 2434–2436.

S. Baj, "Study of the Synthesis of Mixed Dialkyl Peroxides, etc", Journal of Molecular Catalysis A: Chemical 106, (1996), 11–23.

F.H. Dickey, et al "Di–tert–butyl Peroxide and etc.", Industrial and Engineering Chemistry, 1949, 1673–1680.

N.A. Milas, et al "Studies in Organic Peroxides. VIII, etc.", J. Amer. Chem Soc., 1946, 205–208.

Chem Abstract 124:145039, abstracting "Mechanistic Study of the acid catalyzed formation and hydrolysis of MTBE in nonpolar media", *Mol Catal. A: Chem.* 1995, (1), 31–41.

Chem Abstract 70:2925, abstracting "Acid Catalyzed Hydrolysis of ter–butyl methyl ether", *Aust. J. Chem* 1968, 21 (5), 1355–1357.

Chem Abstract 115:91625, abstracting "Catalytic Splitting of methyl tert–butyl ether on fized acids, DECHEMA", *Monogr.* 1991, 11 (Katalyse) 171–188.

Chem Abstract 104:168896, abstracting Selective resin catalyzts for MTBE cleavage, Erdoel Kohle, Erolgas, Petrhchem. 1986,39 (2) 91.

Chem Abstract 100:191363, abstracting JP 59010535 A2 (Jan. 1984).

Derwent WPAT Abstract of DE2400739 (Jul. 17, 1975).

esp@cenet Abstract of EP407840 (Jan. 16, 1991).

esp@cenet Abstract of EP860412 (Aug. 26, 1998).

Derwent WPAT Abstract of JP 03190856, (1991).

* cited by examiner

*Primary Examiner*—Jean F. Vollano
(74) *Attorney, Agent, or Firm*—Daniel Reitenbach

(57) ABSTRACT

A process for production of a t-alkyl peroxide compound includes the steps of:

a) reacting an n-alkyl t-alkyl ether with a reactant mixture comprising an acid catalyst and a compound of the formula $$RO_2H \qquad (I)$$

where R is H or t-alkyl, provided that if R is t-alkyl the t-alkyl peroxide compound product is a di-t-alkyl peroxide, and b) isolating a reaction product comprising said t-alkyl peroxide compound from the mixture resulting from step a).

The process can be used to prepare t-butyl hydroperoxide or di-t-butyl peroxide from methyl t-butyl ether. Sulfuric acid may be used as the acid catalyst.

20 Claims, No Drawings

PREPARATION OF DI-T-ALKYL PEROXIDES AND T-ALKYL HYDROPEROXIDES FROM N-ALKYL ETHERS

FIELD OF THE INVENTION

The present invention is directed to a new synthetic route for making di-t-alkyl peroxides such as di-t-butyl peroxide (DTBP) and t-alkyl hydroperoxides such as t-butyl hydroperoxide (TBHP). In the inventive process an n-alkyl t-alkyl ether, such as methyl t-butyl ether (MTBE), and hydrogen peroxide are used in an acid catalyzed reaction.

BACKGROUND OF THE INVENTION

DTBP is used as initiator in polyethylene production and as a crosslinking agent in wire/cable manufacturing. In U.S. Pat. No. 5,314,511, U.S. Pat. No. 4,406,254 and Coughenour, et al, CHEMTECH 1997 (August) 38–41, DTBP is reported as an effective fuel enhancement additive.

DTBP is most commonly made by reacting TBHP with t-butyl alcohol (TBA) in an aqueous solution using an acid catalyst such as mineral acids (e.g. sulfuric acid, hydrochloric acid), phosphonic acids, p-toluene sulfonic acid, strong acid ion exchange resins (e.g. Amberlyst® 15), heteropolyacids and Lewis acids. References describing such processes include U.S. Pat. No. 4,810,809, U.S. 5,488,176; U.S. 5,288,919; U.S. 5,488,179; U.S. 5,488,178; U.S. 5,345,009; Milas, N. A., et al, *J. Amer. Chem. Soc.,* 1946, 68 (2) 205–208; and Dickey, F. H., et al, *Ind. Eng Chem.* 1949, 41(8) 1673–1679. DTBP is also made commercially by reacting TBA with hydrogen peroxide in the presence of sulfuric acid as a catalyst in a manner as described in Gupta, A. A., et al, "An Improved Process for the Preparation of Di-Tertiary-Butyl Peroxides," IN 173171 (1990). Isobutylene can be used as feed stock instead of TBA as described in U.S. Pat. No. 5,371,298.

An oxidation of isobutane followed by reacting the oxidate in an aqueous solution of an acid catalyst is another known method for the preparation of DTBP, as described in Dickey, et al, *Ind. Eng. Chem.* 1949, 41(8) 1673–1679, in EP 438844 A and in U.S. Pat. No. 5,312,998.

Yet another method for DTBP production includes a reaction of an alkali or alkaline-earth metal salt of TBHP with a t-butyl halide, as described in Dickey, et al, *Ind. Eng Chem.* 1949, 41(8) 1673–1679 and in Baj, S., *J. Mol. Catalysis,* 1996, 106, 11–23.

TBHP is widely used in latex formulation and as an intermediate in manufacturing peroxyesters, peroxyketals and DTBP. Known methods of TBHP synthesis are similar to methods for DTBP synthesis. Documents describing such synthesis include Milas, N. A., et al, *J. Amer. Chem. Soc.,* 1946, 68(2) 205–208; U.S. Pat. No. 5,399,777; EP 639564; U.S. Pat. No. 5,243,084; JP 3/190856 A (1991); Michert, E., *Chem. Stosow.,* 1988 32(1) 171–178; and Milas, N. A., et al, *J. Amer. Chem. Soc.,* 1938, 60 (10) 2434–2436.

Davies, et al,. *J Chem. Soc.* 1958, 4637–4643 describes preparation of certain optically active secondary alkylphenyl hydroperoxides from corresponding alcohols or ethers and hydrogen peroxide.

U.S. Pat. No. 5,866,712 describes use of MTBE as an inert solvent in a process for synthesis of oxalate perester compounds.

SUMMARY OF THE INVENTION

The invention is a process for production of a t-alkyl hydroperoxide or di-t-alkyl peroxide compound comprising the steps of a) reacting an n-alkyl t-alkyl ether with a reactant mixture comprising an acid catalyst and a compound of the formula $$RO_2H \qquad (I)$$

where R is H or t-alkyl, provided that if R is t-alkyl the t-alkyl peroxide compound product is a di-t-alkyl peroxide, b) isolating a reaction product comprising said t-alkyl peroxide compound from the mixture resulting from step a).

The reaction of step a) is preferably performed as a single step reaction. Alternatively, however, it may be broken into two steps, a hydrolysis reaction of the ether in the presence of the acid catalyst, followed by in situ addition of, and reaction with, $RO_2H$.

Product yields are affected by reactant ratios and other process parameters. Preferred process parameters comprise further aspects of the invention.

DETAILED DESCRIPTION OF THE INVENTION

The entire disclosures of all US patents and other published documents and any copending US patent applications mentioned anywhere herein are expressly incorporated herein by reference.

It has been discovered that t-alkyl peroxides, such as DTBP and TBHP can be readily produced in high yield from corresponding n-alkyl t-alkyl ethers such as MTBE. The inventive process is especially advantageous for the production of DTBP.

The process can also be applied to preparation of other di-t-alkyl peroxides and t-alkyl hydroperoxides.

n-Alkyl t-alkyl ethers can be cleaved or hydrolyzed into the mixture of corresponding alcohols (aqueous solutions) or alkanol and t-olefins (non-aqueous solutions) in the presence of an acidic catalyst. Known catalysts for such reactions include inorganic and organic acids, acidic ion-exchange resins, Lewis acids, heteropolyacids, etc. Some olefins are produced according to this methodology and previous work attempting to synthesize a t-amyl alcohol from t-amyl methyl ether did not go to completion due to a product/reactant equilibrium which when shifted by distilling out methanol resulted in the dehydration of the t-amyl alcohol product to isoamylene.

The present invention avoids the problems encountered in isolating the t-alkyl alcohol product of acid catalyzed hydrolysis of t-alkyl ethers This is accomplished by performing the hydrolysis/peroxidization reactions in situ, that is without isolation of an alcohol intermediate.

While the following description is made primarily with reference to preparation of DTBP and TBHP from MTBE, it should be understood that the process described and illustrated is applicable to preparation of these or other di-t-alkyl peroxides and t-alkyl hydroperoxides by substituting corresponding n-alkyl t-alkyl ethers for MTBE. With respect to the ethers which may be used in the inventive process, the n-alkyl portion thereof suitably may have 1–4 carbon atoms, preferably 1–2 carbon atoms, and the t-alkyl portion thereof suitably may have from 4 to about 10 carbon atoms, preferably 4–6 carbon atoms. Examples of suitable n-alkyl t-alkyl ethers include MTBE, methyl t-amyl ether, methyl t-hexyl ether, ethyl t-butyl ether, ethyl t-amyl ether, ethyl t-hexyl ether, n-propyl t-butyl ether, n-propyl t-amyl ether, and n-propyl t-hexyl ether.

In formula (I), above, R may be H for syntheses of either a t-alkyl hydroperoxide or di-t-alkyl peroxide, such that the compound $RO_2H$ is hydrogen peroxide. For the preparation of di-t-alkyl peroxide, however, R may alternatively be t-alkyl (suitably having from 4 to 10 carbon atoms), such that the compound $RO_2H$ is a t-alkyl hydroperoxide. Hydrogen peroxide is generally suitable for synthesis of both t-alkyl hydroperoxides and symmetric di-t-alkyl peroxides compounds. A process of the invention using t-alkyl n-alkyl ether and t-alkyl hydroperoxide reactants in which the respective reactants have different t-alkyl groups effects the preparation of asymmetric di-t-alkyl peroxides.

Generally, the ratio of the $RO_2H$ compound of formula (I) to the ether reactant may be from about 0.3 to about 5, on a mole basis. The product yield, as between DTBP and TBHP using hydrogen peroxide as the compound $RO_2H$, is determined primarily by stoichiometric ratio of ether to hydrogen peroxide. In general, DTBP is the predominant product at $H_2O_2$/MTBE mole ratios below about 0.7. TBHP is predominant at $H_2O_2$/MTBE mole ratios above 1. Preferred $H_2O_2$/MTBE ratios for preparation of DTBP are in the range of from 0.4–0.6. For TBHP, the $H_2O_2$/MTBE ratio is preferably in the range of 1.5–3.

An acid is used as catalyst in the reaction. Acid catalysts may be inorganic acids, organic acids, acidic ion-exchange resins (for instance Amberlyst® 15 ion exchange resin), Lewis acids, heteropolyacids (for instance phosphotungstic), etc. Suitably the acid is a mineral acid such as sulfuric, hydrochloric or nitric acid. Sulfonic acids such as methane sulfonic and p-toluene sulfonic acids are further examples of acids which may be used as the catalyst. Sulfuric acid is particularly suitable. Preferred $H_2SO_4$/MTBE mole ratios are in the range of 0.4–0.6.

Water is desirable in the reaction mixture, suitably in an amount of at least one mole $H_2O$ per mole MTBE. Some or all of the water content may be provided by use of aqueous solutions of the reactants. Additional water may be provided as needed for safety (e.g. to lower the exotherm or to allow use of dilute reactants) or to optimize yields. For DTBP production, a suitable total water content in the reaction mixture, may be from about 1 to about 3, preferably 1.5–2.5, moles $H_2O$ per mole MTBE.

In general suitable reaction temperatures range from about 20° C. to about 70° C. Ambient pressures are suitable. Pressures higher or lower than ambient pressure also may be acceptable.

Isolation and purification of the product may be accomplished in the same manner as for recovery of such products from reaction of alcohols and hydrogen peroxide or t-alkyl hydroperoxides. A suitable recovery scheme involves separation from the acid catalyst, neutralization of any residual acid, washing with water and drying.

The invention is illustrated by the following non-limiting examples where percentages are given on a weight basis.

EXAMPLES

Example 1

Production of TBHP

Into a 250 ml round bottom three neck flask (equipped with an agitator, thermometer, and pressure equalizing addition funnel), 40 g MTBE was placed.

Sufficient $H_2SO_4$ (as 55% solution in water) was added to provide a mole ratio of $H_2SO_4$/MTBE of 0.5/1.0, and the mixture at 45° C. was stirred for 1 hour. Then $H_2O_2$ (as 60% solution in water) was added in an amount which provided a mole ratio of $H_2O_2$/MTBE of 2.0/1.0. The mixture was stirred while maintaining the reaction temperature at 45° C. for an additional hour. When the reaction time was up, the reaction mixture was cooled down to 20° C. and transferred to a tared 250 ml separatory funnel. The aqueous phase was removed. The product was neutralized to pH 7 with a few drops of 25% NaOH in order to remove residual acid and hydrogen peroxide, after which the aqueous phase was removed and the product was weighed and analyzed. TBHP was obtained in 63.5% yield at a purity of 75.4%.

Example 2

Production of TBHP

The procedure of Example 1 was repeated except that the addition of the $H_2SO_4$ was followed immediately with the addition of the $H_2O_2$, with a total reaction time of one hour. TBHP was obtained in 67.4% yield at a purity of 75.9%.

Example 3

Production of TBHP

The procedure of Example 2 was repeated except that the reaction temperature was maintained at 50° C. TBHP was obtained in 69.6% yield at a purity of 76.7%.

Example 4

Production of TBHP

The procedure of Example 2 was repeated except that the amount of hydrogen peroxide added relative to the MTBE content gave a mole basis ratio of 2.5/1.0. TBHP was obtained in 69.5% yield at a purity of 78.4%.

In the following examples all references to $H_2O$ ratios are to the total water added from all sources.

Example 5

Production of DBTP

Into a 250 ml round bottom three neck flask (equipped with an agitator, thermometer, and pressure equalizing addition funnel), 40 g MTBE was placed; and sufficient $H_2SO_4$ aqueous solution, $H_2O_2$ (as 60% solution in water) and water were added to provide a mole ratio of MTBE/$H_2SO_4$/$H_2O_2$/$H_2O$ of 2.15/1.3/1.0/6.3. The mixture was stirred at 50° C. two hours. When the reaction time was up, the reaction mixture was cooled down to 20° C., and transferred to a tared 250 ml separatory funnel. The aqueous phase was removed. The product was neutralized to pH 7 with 25% NaOH in order to remove residual acid and hydrogen peroxide, after which the aqueous phase was removed and the product was washed 2–3 times with 150 ml cold water, weighed and analyzed. DTBP was obtained in 75.4% yield at a purity of 87.0%.

Example 6

Production of DBTP

Example 5 was repeated except that the relative mole ratio of MTBE/$H_2SO_4$/$H_2O_2$/$H_2O$ employed was 2.15/1.3/1.0/3.3. DTBP was obtained in 94.0% yield at a purity of 96.1%.

Example 7

Production of DBTP

Example 5 was repeated except that the relative mole ratio of MTBE/$H_2SO_4$/$H_2O_2$/$H_2O$ employed was 2.0/1.3/1.0/3.3. DTBP was obtained in 90.5% yield at a purity of 98.1%. The product was then purged with nitrogen at 55° C. for 1 hour and reanalyzed. The purity of the product after purging was 99.6%.

As can be seen from the foregoing examples TBHP of a quality acceptable for many commercial applications, for instance for the production of peroxyketals, can be produced by the inventive method and DTBP can be produced by the method at a purity which meets current commercial standards. Moreover the process times are faster than is currently required to obtain this product from t-butyl alcohol and hydrogen peroxide and the raw material cost of MTBE is lower than that of t-butyl alcohol.

In similar manner, although optimal conditions may vary, hydrogen peroxide may be reacted with methyl t-amyl ether to provide t-amyl hydroperoxide or di-t-amyl peroxide; with methyl t-hexyl ether to provide t-hexyl hydroperoxide or di-t-hexyl peroxide; with ethyl t-butyl ether to provide t-butyl hydroperoxide or di-t-butyl peroxide; with ethyl t-amyl ether to provide t-amyl hydroperoxide or di-t-amyl peroxide; with ethyl t-hexyl ether to provide t-hexyl hydroperoxide or di-t-hexyl peroxide; with n-propyl t-butyl ether to provide t-butyl hydroperoxide or di-t-butyl peroxide; with n-propyl t-amyl ether to provide t-amyl hydroperoxide or di t-amyl peroxide; or with n-propyl t-hexyl ether to provide t-hexyl hydroperoxide or di-t-hexyl peroxide. Illustrative of reactions employing hydroperoxide reactants are the reaction of t-butyl hydroperoxide with methyl t-butyl ether to provide di-t-butyl peroxide; the reaction of t-hexyl hydroperoxide with methyl t-hexyl ether to provide di-t-hexyl peroxide; the reaction of t-butyl hydroperoxide with methyl t-amyl ether to provide t-butyl t-amyl peroxide; the reaction of t-butyl hydroperoxide with methyl t-hexyl ether to provide t-butyl t-hexyl peroxide; and the reaction of t-amyl hydroperoxide with ethyl t-hexyl ether to provide t-amyl t-hexyl peroxide.

The above Examples and disclosure are intended to be illustrative and not exhaustive. These examples and description will suggest many variations and alternatives to one of ordinary skill in this art. All these alternatives and variations are intended to be included within the scope of the attached claims. Moreover, all possible alternative dependent combinations of the features recited in the dependent claims, whether written in multiple dependent form or not, should be considered to be within the scope of the invention. Those familiar with the art may recognize other equivalents to the specific embodiments described herein which equivalents are also intended to be encompassed by the claims attached hereto. It should also be understood that, in addition to those combinations recited in the dependent claims, all other possible combinations of the features of the dependent claims are considered to be specific aspects of the invention.

What is clamed is:

1. A process for production of a t-alkyl peroxide compound selected from t-alkyl hydroperoxides and di-t-alkyl peroxides, the process comprising the steps of
   a) reacting in-situ an n-alkyl t-alkyl ether with a reactant mixture comprising an acid catalyst and a compound of the formula

where R is H or t-alkyl, provided that if R is t-alkyl the t-alkyl peroxide compound product is a di-t-alkyl peroxide, and
   b) isolating a reaction product comprising said t-alkyl peroxide compound from the mixture resulting from step a).

2. A process as in claim 1 wherein said n-alkyl t-alkyl ether is selected from the group consisting of methyl t-butyl ether, methyl t-amyl ether, methyl t-hexyl ether, ethyl t-butyl ether, ethyl t-amyl ether, ethyl t-hexyl ether, propyl t-butyl ether, propyl t-amyl ether and propyl t-hexyl ether.

3. A process as in claim 1 wherein said n-alkyl t-alkyl ether is methyl t-butyl ether.

4. A process as in claim 1 wherein said t-alkyl peroxide compound is a di-t-alkyl peroxide, said compound RO$_2$H is hydrogen peroxide, and hydrogen peroxide is used in step a) in an amount of 0.4–0.6 moles hydrogen peroxide per mole of n-alkyl t-alkyl ether.

5. A process as in claim 4 wherein in step a) sulfuric acid is used as said acid catalyst in an amount of 0.4–0.6 moles sulfuric acid per mole of n-alkyl t-alkyl ether used in step a).

6. A process as in claim 4 wherein in step a), water is also used in a total amount of about 1.5–2.5 moles water per mole n-alkyl t-alkyl ether.

7. A process as in claim 1 wherein in step a) a reaction temperature of about 20° C. to about 70° C. is used.

8. A process as in claim 3 wherein said t-alkyl peroxide compound is a t-alkyl hydroperoxide.

9. A process as in claim 8 wherein said compound RO$_2$H is hydrogen peroxide and hydrogen peroxide is used in step a) in an amount of 1.5–3 moles hydrogen peroxide per mole of n-alkyl t-alkyl ether.

10. A process as in claim 9 wherein in step a) sulfuric acid is used as said acid catalyst in an amount of about 0.4 to about 0.6 moles sulfuric acid per mole of n-alkyl t-alkyl ether.

11. A process as in claim 10 wherein in step a), water is also used.

12. A process as in claim 1 wherein said acid catalyst is an inorganic or organic acid, an acidic ion-exchange resin, a Lewis acid, or a heteropolyacid.

13. A process as in claim 1 wherein said acid catalyst is selected from the group consisting of sulfuric, hydrochloric and nitric acids.

14. A process as in claim 1 wherein the n-alkyl group of said n-alkyl t-alkyl ether has one to four carbon atoms and the t-alkyl group thereof has four to ten carbon atoms.

15. A process as in claim 1 wherein said t-alkyl peroxide compound is a di-t-alkyl peroxide and said compound RO$_2$H is a t-alkyl hydroperoxide.

16. A process for production of an asymmetric di-t-alkyl peroxide compound the process comprising the steps of
    a) reacting an n-alkyl t-alkyl ether with a reactant mixture comprising an acid catalyst and a compound of the formula

where R is t-alkyl, and
    b) isolating a reaction product comprising said asymmetric t-alkyl peroxide compound from the mixture resulting from step a).

17. A process as in claim 1 wherein said t-alkyl peroxide compound is di-t-butyl peroxide or t-butyl hydroperoxide.

18. A process as in claim 1 wherein the reaction product is a di-t-alkyl peroxide and the compound of formula (I) is selected from the group consisting of t-butyl hydroperoxide, t-amyl hydroperoxide and t-hexyl hydroperoxide.

19. A process as in claim 1 wherein the in-situ reacting step a) comprises first mixing and reacting the n-alkyl-t-alkyl ether with said acid catalyst in a hydrolysis reaction, and then, without isolating an intermediate product, adding the compound of formula (I) to the reaction mixture and continuing the reaction to obtain said t-alkyl peroxide compound.

20. A process as in claim 1 wherein the in-situ reaction step comprises substantially concurrently mixing said ether, said acid catalyst and the compound of formula (I), then reacting the mixture to obtain said t-alkyl peroxide compound.

* * * * *